US00PP37050P2

(12) United States Plant Patent
Schoone

(10) Patent No.: US PP37,050 P2
(45) Date of Patent: Oct. 21, 2025

(54) ***PHALAENOPSIS* PLANT NAMED 'Keynote'**

(50) Latin Name: *Phalaenopsis hybrida*
Varietal Denomination: Keynote

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/171,330

(22) Filed: Apr. 6, 2025

Related U.S. Application Data

(60) Provisional application No. 63/575,712, filed on Apr. 6, 2024.

(51) Int. Cl.
*A01H 5/02* (2018.01)
*A01H 6/62* (2018.01)

(52) U.S. Cl.
USPC ..... Plt./311

CPC ..... *A01H 6/62* (2018.05); *A01H 5/02* (2013.01)

(58) Field of Classification Search
USPC ..... Plt./263.1, 311
See application file for complete search history.

(56) References Cited

U.S. PATENT DOCUMENTS

PP36,582 P3 * 4/2025 Schoone ..... A01H 6/62 Plt./311

* cited by examiner

*Primary Examiner* — Karen M Redden
(74) *Attorney, Agent, or Firm* — C. Anne Whealy

(57) ABSTRACT

A new and distinct cultivar of *Phalaenopsis* plant named 'Keynote', characterized by its upright plant habit; strong flowering stems; healthy and sturdy leaves; freely flowering habit with typically two inflorescences developing per plant, each inflorescence with numerous flowers; "big lip" type flowers with light purple-colored petals, labella and sepals with reddish purple-colored venation; and good postproduction longevity.

2 Drawing Sheets

Figure 1:
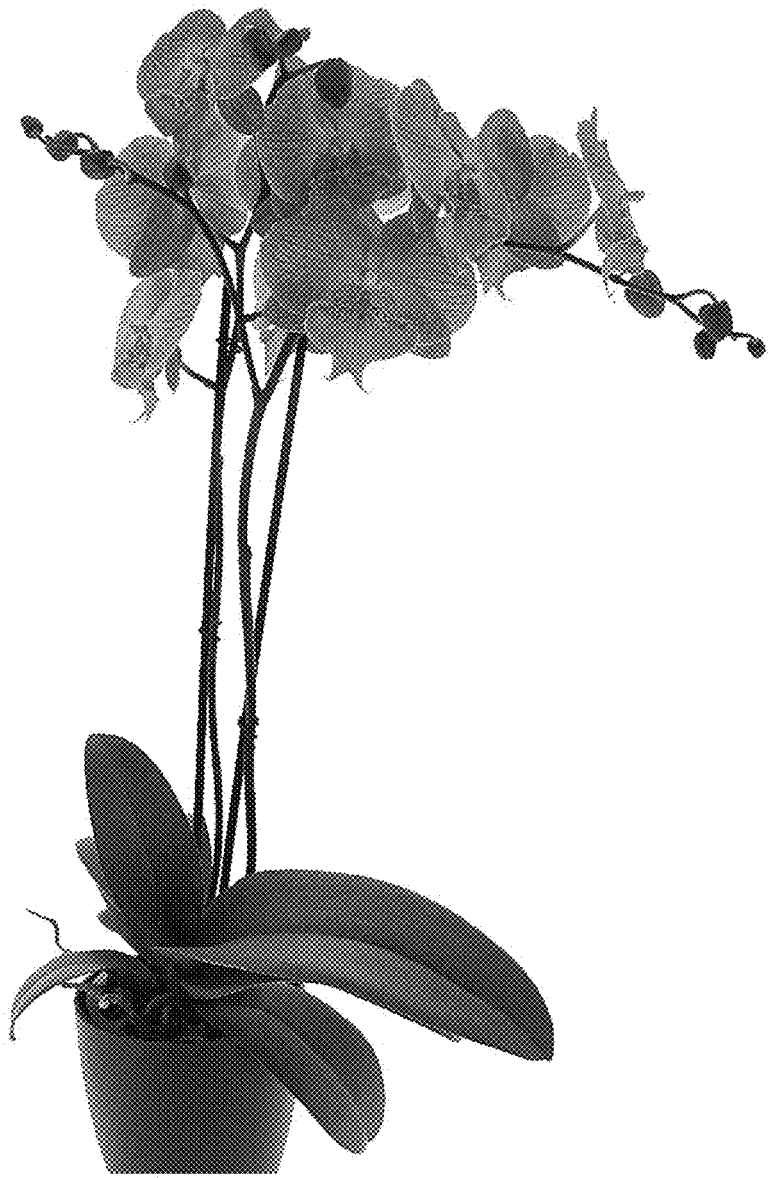

Botanical designation: *Phalaenopsis hybrida.*
Cultivar denomination: 'KEYNOTE'.

CROSS-REFERENCED TO CLOSELY-RELATED APPLICATIONS

Title: Varieties of *Phalaenopsis* Plants
Inventor: René Schoone
Filed: Apr. 6, 2024
Ser. No. 63/575,712

Inventor and Applicant/Assignee hereby claims the benefit of this provisional U.S. Patent Application.

A European Community Plant Breeder's Rights application for the instant plant was filed by the Applicant/Assignee, Floricultura B.V. of Heemskerk, The Netherlands on Oct. 9, 2024, application number 2024/2360. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Keynote'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May 2014 in Assendelft, The Netherlands of a *Phalaenopsis hybrida* 'K.S. Big Class', not patented, as the female, or seed, parent with *Phalaenopsis hybrida* 'Yushan Mongo', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October 2020.

Asexual reproduction of the new *Phalaenopsis* plant by in vitro meristem propagation in a controlled environment in Assendelft, The Netherlands since September 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Keynote'. These characteristics in combination distinguish 'Keynote' as a new and distinct *Phalaenopsis* plant:

1. Upright plant habit.
2. Strong flowering stems.
3. Healthy and sturdy leaves.

4. Freely flowering habit with typically two inflorescences developing per plant, each inflorescence with numerous flowers.
5. "Big lip" type flowers with light purple-colored petals, labella and sepals with reddish purple-colored venation.
6. Good postproduction longevity.

Plants of the new *Phalaenopsis* can be compared to plants of the female parent, 'K.S. Big Class'. Plants of the new *Phalaenopsis* differ primarily from plants of 'K.S. Big Class' in flower coloration as the flower petals of plants of the new *Phalaenopsis* have small dots at the base whereas flower petals of plants of 'K.S. Big Class' do not have any spots. In addition, the "big lip" labella of plants of the new *Phalaenopsis* have larger spots than the "big lip" labella of plants of 'K.S. Big Class'.

Plants of the new *Phalaenopsis* can be compared to plants of the male parent, 'Yushan Mongo'. Plants of the new *Phalaenopsis* differ primarily from plants of 'Yushan Mongo' in flower petal arrangement and color as flower petals of plants of the new *Phalaenopsis* are touching and imbricate whereas flower petals of plants of 'Yushan Mongo' are free and not imbricate. In addition, the ground color of the flower petals of plants of the new *Phalaenopsis* is light purple whereas the ground color of the flower petals of 'Yushan Mongo' is white.

Plants of the new *Phalaenopsis* can be compared to plants of *Phalaenopsis hybrida* 'Gentle Whistler', not patented. In side-by-side comparisons, plants of the new *Phalaenopsis* differ primarily from plants of 'Gentle Whistler' in the following characteristics:

1. Plants of the new *Phalaenopsis* are shorter than plants of 'Gentle Whistler'.
2. Flowers of plants of the new *Phalaenopsis* are not as broad as flowers of plants of 'Gentle Whistler'.
3. Flower petals of plants of the new *Phalaenopsis* are more imbricate than flower petals of plants of 'Gentle Whistler'.
4. Flower petals of plants of the new *Phalaenopsis* have small dots at the base whereas flower petals of plants of 'Gentle Whistler' do not have any spots.
5. The new *Phalaenopsis* and 'Gentle Whistler' differ in flower petal color as the ground color of flower petals of plants of the new *Phalaenopsis* is light purple whereas the ground color of the flower petals of 'Gentle Whistler' is white.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Keynote' grown in a container.

Figure 2:
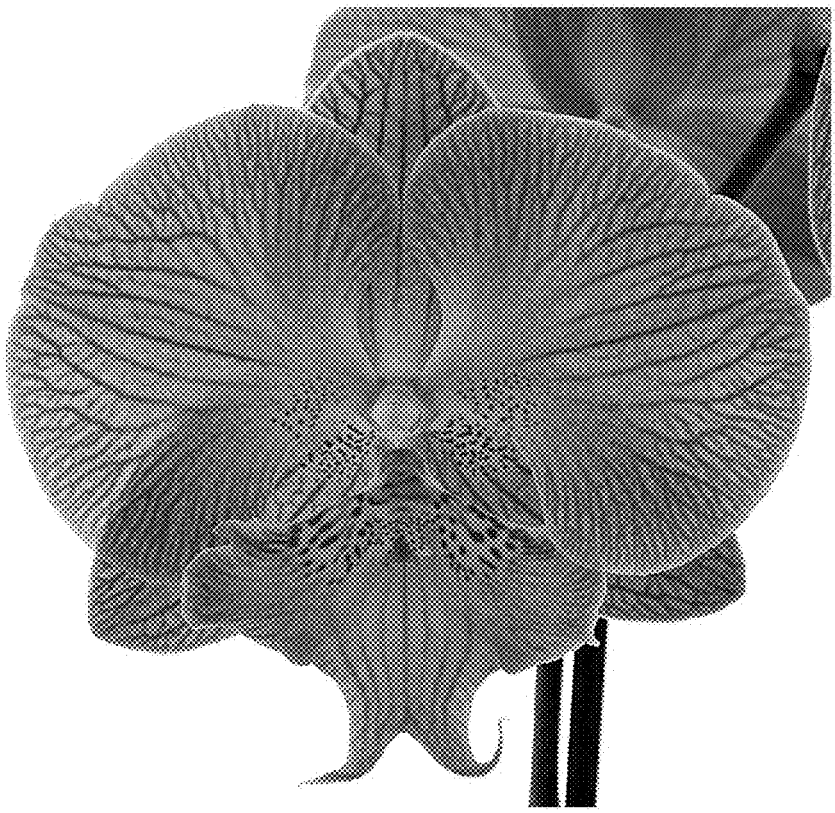

The photograph on the second sheet (FIG. 2) is a close-up view of a typical flower of 'Keynote'.

DETAILED BOTANICAL DESCRIPTION

The aforementioned photographs and following observations and measurements describe plants grown during the summer in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Keynote'.

Parentage:

*Female, or seed, parent.*—*Phalaenopsis hybrida* 'K.S. Big Class', not patented.

*Male, or pollen, parent.*—*Phalaenopsis hybrida* 'Yushan Mongo', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane.*—About 12.5 cm.

*Plant height, substrate level to top of floral plane.*—About 50.1 cm.

*Plant diameter or spread.*—About 36.4 cm.

Leaf description:

*Arrangement and quantity.*—Distichous, simple; sessile; about six to seven fully-developed leaves per plant.

*Length.*—About 23 cm.

*Width.*—About 8.1 cm.

*Aspect.*—Semi-erect and outwardly arching.

*Shape.*—Narrowly elliptic to elliptic-oblong; slightly carinate.

*Apex.*—Unequal acute to unequal obtuse.

*Base.*—Sheathing. Sheath length: About 1.8 cm. Sheath width: About 1.6 cm. Sheath color, upper and lower surfaces: Close to 143A; distal margins, close to N186C.

*Margin.*—Entire.

*Texture and luster, upper surface.*—Smooth, glabrous; slightly glossy.

*Texture and luster, lower surface.*—Smooth, glabrous; moderately glossy.

*Venation pattern.*—Camptodromous.

*Color.*—Developing leaves, upper surface: Close to a blend of close to NN137A and 146A; narrow marginal edges, close to 187C. Developing leaves, lower surface: Close to 146B slightly tinged with close to a blend of N186C and 200A; marginal edges, close to a blend of N186C and N200A. Fully expanded leaves, upper surface: Close to NN137B; venation, close to 147A. Fully expanded leaves, lower surface: Close to 146B slightly tinged with close to a blend of N186C and 200A; marginal edges, close to a blend of N186C and N200A; venation, close to N200A.

Inflorescence description:

*Appearance and flowering habit*.—Showy zygomorphic flowers arranged on axillary simple or branched racemes; typically two inflorescences develop per plant; each inflorescence with about 14 flowers; flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about seven weeks on the plant; flowers not persistent.

*Inflorescence length* (*lowermost flower to inflorescence apex*).—About 31.2 cm.

*Inflorescence width*.—About 15.8 cm.

*Flower buds*.—Height: About 2.1 cm. Diameter: About 1.6 cm by 1.7 cm. Shape: Broadly ovate. Color: Close to N77B; at the base, tinged with close to N148B; venation, close to N186C.

*Flower size*.—About 10.2 cm (vertical) by 10.6 cm (horizontal).

*Flower depth*.—About 2.1 cm.

*Petals, quantity and arrangement*.—Three, two lateral petals and one center petal transformed into a labellum.

*Lateral petals*.—Length: About 5 cm. Width: About 6.5 cm. Shape: Broadly reniform to close to broadly lunate; not fused. Apex: Obtuse. Margin: Entire to slightly and irregularly angulate; occasionally with random shallow incisions. Texture and luster, upper and lower surfaces: Smooth, glabrous; moderately velvety; matte. Color: When opening, upper surface: Close to N78C and N78D; towards the base, close to 76C; at the base, close to N78B to N78C with small dots, close to N78B; venation, close to N78A. When opening, lower surface: Close to N78D; towards the base, close to 77D; at the base, tinged with close to 153D; venation, close to NN78B. Fully opened, upper surface: Close to a blend of N81D and 84B; towards the base, close to 84D; at the base, close to N78C with small dots, close to N78B; venation, close to NN78B. Fully opened, lower surface: Close to N80D; towards the center, close to 76B; marginal edges, close to 76B; venation, close to NN78B.

*Labella*.—Appearance: Lateral and central lobes fused forming a "big lip" type labella. Length: About 5 cm. Width: About 6.2 cm. Shape: Rhomboidal-deltoid in overall outline; slightly concave. Apex: Cleft with two cirrhose apices. Margins: Entire. Texture and luster, upper and lower surfaces: Smooth, glabrous, moderately velvety; matte. Callosities: Located at the base of the labellum and attachment point of the lateral petals; about 4 mm in length, about 8 mm in width and about 9 mm in height. Color: When opening, upper surface: Close to N78D; lower half of lateral lobes, close to NN155B; dots and stripes along venation, close to 71A and 71B; venation, close to N78B. When opening, lower surface: Close to N78C and N78D; at the base, close to 155C; venation, close to N78B. Fully opened, upper surface: Close to a blend of N81D and 84B; lower half of lateral lobes, close to NN155D; dots and stripes along venation, close to 72A and 72B; venation, close to NN78B. Fully opened, lower surface: Close to N78D; at the base, close to NN155C; venation, close to N78B and N78C. Color, callosities: When developing: Close to 150C, 150D and 181D; fine dots, close to 181B. Fully developed: Close to N155B, 156A and 181D; fine dots, close to 181C.

*Sepals*.—Quantity and arrangement: Three, one upper dorsal sepal and two lower lateral sepals. Length, dorsal sepal: About 5.4 cm. Width, dorsal sepal: About 3.7 cm. Length, lateral sepals: About 5.5 cm. Width, lateral sepals: About 3.4 cm. Shape, dorsal sepal: Elliptic. Shape, lateral sepals: Ovate. Apex, dorsal sepal: Obtuse to shallowly retuse. Apex, lateral sepals: Acute. Base, dorsal and lateral sepals: Truncate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to N78C and N78D; venation, close to N78A. When opening, lower surface: Close to 186B; towards the margins, close to N78C; venation, close to a blend of N78B and NN78B. Fully opened, upper surface: Close to a blend of N81D and 84B; towards the base, close to 84D; marginal edges, close to 76B; venation, close to NN78B. Fully opened, lower surface: Close to NN74D; towards the margins, close to N78C; venation, close to a blend of N78B and NN78B. Color, lateral sepals: When opening, upper surface: Close to N78D; towards the base, close to N80D; at the base, small blotch, close to 150D; small dots, close to 71A; venation, close to a blend of N78A and NN78A. When opening, lower surface: Close to 186B; towards the base, close to 186C; towards the margins, close to 70B; at the base, small blotch, close to 146D. Fully opened, upper surface: Close to N78D; at the base, small blotch, close to 157C with dots, close to 72A; venation, close to a blend of N78A and NN78B. Fully opened, lower surface: Close to N78D; towards the center, close to 75A; at the base, small blotch, close to 152D.

*Peduncles*.—Length: About 59.9 cm. Diameter: About 6 mm. Strength: Strong. Aspect: Upright to outwardly arching. Texture and luster: Smooth, glabrous; matte. Color: Close to a blend of 147A and N189A densely covered with fine dots, close to 146D.

*Pedicels*.—Length: About 5.1 cm. Diameter: About 3 mm. Strength: Moderately strong. Aspect: About 60° from peduncle axis. Texture and luster: Smooth, glabrous; matte. Color: Close to N148C; distal end, close to 84C; proximal end, close to a blend of 148A and 197A.

*Reproductive organs*.—Androecium: Column length: About 9 mm. Column width: About 6 mm. Column color: Close to NN78D; distally, close to NN155A. Pollinia quantity: Two. Pollinia diameter (per two pollinia): About 2.5 mm. Pollinia color: Close to 23A. Gynoecium: Stigma length: About 3 mm. Stigma width: About 4 mm. Stigma shape: Reniform. Stigma color: Close to N155A. Ovary length: About 9 mm. Ovary diameter: About 1 mm. Ovary color: Close to 150C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Keynote' as herein illustrated and described.

* * * * *